(12) United States Patent
Eugster et al.

(10) Patent No.: US 6,420,614 B1
(45) Date of Patent: Jul. 16, 2002

(54) PROCESS FOR OBTAINING 3'-EPILUTEIN

(75) Inventors: Conrad Hans Eugster, Walliselen (CH); Ricardo Montoya-Olvera; José-Odon Torres-Quiroga, both of Nuevo León (MX)

(73) Assignee: Industrial Organica, S.A. DE C.V., Monterrey (MX)

( * ) Notice: Subject to any disclaimer, the term of this patent is extended or adjusted under 35 U.S.C. 154(b) by 0 days.

(21) Appl. No.: 09/685,321

(22) Filed: Oct. 10, 2000

(51) Int. Cl.[7] ................................................ C07C 35/21

(52) U.S. Cl. ....................................................... 568/816

(58) Field of Search ................................. 568/824, 816

(56) References Cited

U.S. PATENT DOCUMENTS 5,523,494 A * 6/1996 Torres-Cardona ........... 568/834

* cited by examiner

*Primary Examiner*—Michael L. Shippen
(74) *Attorney, Agent, or Firm*—Abelman, Frayne & Schwab

(57) ABSTRACT

A process for obtaining 3'-epilutein, by epimerization of a lutein-containing extract with an aqueous solution of a strong organic acid which is slowly added under agitation at room temperature, in the presence of an organic aprotic media, to obtain 3'-epilutein(crystals) in a solution which is neutralized with an alkali and extracting the 3'-epilutein from said solution by means of an organic media, then washing and drying the crystals and purifying them by chromatography by means of a chromatography column.

26 Claims, 2 Drawing Sheets

PROCESS FOR OBTAINING 3'-EPILUTEIN

BACKGROUND OF THE INVENTION

1. Field of the Invention

This invention refers to a process for obtaining epilutein and, more specifically to a process for obtaining 3'-epilutein from lutein-containing extracts, and to a process for the production of optically active zeaxanthin from said 3'-epilutein.

2. Description of the Related Art

More than 50 years have elapsed since Karrer & Jucker published an article in *Helv. Chim. Acta* 30, 266 (1949) with respect to the first isomerization of an epsilon-endgroup in a carotenoid molecule into one with a beta-endgroup with the aid of a strong alkali. This includes an extension of the length of the polyene-chain from originally 10 to 11 conjugated double bonds, as illustrated in FIG. 1 of the enclosed drawings.

However, only a few of the scientific laboratories in the world realized the importance of this invention, and so, the reaction generally fell into oblivion, and was regarded merely as a curiosity. In recent times the situation has changed drastically, mainly because of the following reasons:

1. The recognition of the general importance of the carotenoids as colorants for animal tissues either by ingestion from natural sources or from food additives [J. C. Bauernfeind, G. B. Brubacher, H. M. Kläui, W. L. Marusich, "*Use of Carotenoids*", in "*Carotenoids*"(Ed. O. Isler, H. Gutmann, U. Solms), Birkhäuser, Basel, 1971, Pag. 743,ff; J. C. Bauernfeind (ed), "*Carotenoids as Colorants and Vitamin A Precursors*", Academic Press, N.Y. 1981; K. Schiedt, "*Absorption and Metabolism in Birds, Fish and Crustaceans*", in "*Carotenoids*", Ed. G. Britton, S. Liaaen-Jensen, H. Pfander, Vol. 3: *Biosynthesis and Metabolism*" Birkhäuser, Basel, 1998, pag. 285, ff].

2. Significant progress in the experimental and practical handling of the epsilon-beta-arrangement (U.S. Pat. No. 5,523,494 issued Jun. 4, 1996 to Torres-Cardona et al., see also chronological survey of relevant references in this reference).

The situation today shows a fairly good and industrially useful conversion of lutein (I) (see FIG. 1) into a stereoisomer of zeaxanthin which itself proves to be a better colorant than lutein (I), e.g. for broilers and shrimps. This is very important because lutein is found in abundant quantities in yellow flowers and in all green leaves.

However, a main disadvantage of this rearrangement exists in the stereochemical situation: lutein from plant sources always has the (3R,3'R.6'R)-chirality [R. Buchecker, C. H. Eugster, *Chimia*, 25, 192 (1971)] as shown in formula I at FIG. 1. Therefore, zeaxanthin prepared from lutein necessarily has the (3R,3'S)-chirality as depicted in II (see FIG. 2) and, consequently, is the meso-form [R. Buchecker, P. Hamm, C. H. Eugster, *Chimia*, 26, 134 (1972); A. G. Andrewes, G. Borch, S. Liaaen-Jensen, *Acta Chem. Scand.* B28,139 (1974)]. A trifling quantity of (3R,3'R)-zeaxanthin found in zeaxanthin prepared from lutein is derived from optically active zeaxanthin which naturally accompanies lutein in Tagetes, [U.S. Pat. No. 5,780,693 issued Jul. 14, 1998 to Bernhard K. et al.] and is not a product of an epimerization.

The main disadvantage of meso-zeaxanthin is caused by its lower potency in pigmenting of egg yolk, as shown by the following references: K. Schiedt, "*Absorption and Metabolism in Birds, Fish and Crustaceans*", in *Carotenoids*", (Ed. G. Britton, S. Liaaen-Jensen, H. Pfander), Vol. 3: *Biosynthesis and Metabolism*", Birkhäuser, Basel, 1998, pag. 285 ff., and H. Hencken, *Poultry Science*, 71, 711–717, (1992):

| (3R, 3'R)-zeaxanthin (III) | 100% |
|---|---|
| (3RS, 3'SR)-zeaxanthin (racemic) | 92% |
| (3S, 3'S)-zeaxanthin (enantiomer) | 86% |
| (3R, 3'S)-zeaxanthin (meso, II) | 37% |

On the other hand, Garnett et al, U.S. Pat. No. 5,747,544 issued May 5, 1998, discloses the convenience of obtaining (3R-3'R) stereoisomers of zeaxanthin, for treating or preventing retinal degeneration in humans, by administering a drug formulation containing said (3R-3'R) stereoisomers of zeaxanthin in a carrier substance.

From these results, there followed the necessity of developing a procedure to obtain optically-active III from lutein (I).

The conversion of meso-zeaxanthin into III (see FIG. 3), or the racemate or the (3S,3'S)-zeaxanthin, to applicants knowledge, has no precedent, and no such publication has been found in the literature. It would require a selective protection of one of the two OH-groups, e.g. by acetylation followed by an enzymic hydrolysis. This, hopefully, could lead to 25% of the desired product at best.

Otherwise, instead of enzymic reaction, an inversion of the stereochemistry at the unprotected OH-group could be envisaged, e.g. by an Mitsunobu-reaction. However, the necessary reagents are costly and further, the yields in this reaction are usually low; see hereafter.

Accordingly, Applicants could not see the purpose of expending time and effort in the experimental testing of such a reaction.

Another remarkable way is described by Sanroma et al. (U.S. Pat. No. 5,998,678 issued Dec. 7, 1999 to Sanroma et al.) which mentions the oxidation of meso-zeaxanthin (II) into the dioxocompound IV (see FIG. 4) followed by a hydride reduction into the mixture of II and racemic zeaxanthin. Applicants do not see recommendable this multi-step sequence, mainly because they do not see a more efficient way to carry it out, as discussed below.

In further reflecting on these problems with racemic zeaxanthin, applicants focused on 3'-epilutein (V, see FIG. 5) as a possibly excellent starting material for the preparation of optically active (3R,3'R)-zeaxanthin (III), provided it also permitted one to carry on the epsilon-beta-rearrangement with alkali.

Overview of the Occurrence of 3'-epilutein in Nature and of the Preparation of 3'-epilutein A search in libraries and in data banks proved that the occurrence of 3'-epilutein in plants is extremely rare.

Until the present time, it has only been detected in the following: flowers of *Caltha palustris* [A. G. Dabbagh, K. Egger, Zeitschr. *Pflanzenphysiol.* 72, 177 (1974)], anthers of roses and peonies [E. Marki-Fischer, C. H. Eugster, *Helv. Chim. Acta* 37, 1205 (1990)], and flowers of Tagetes [F. Khachik, A. Steck, H. Pfander; *J. Agric. Food Chem.* 47,455 (1999)].

It occurs partly in esterified form. Common by-products are carotenes and carotenoles. From this, it follows that plants do not offer a reasonable source for the preparative isolation of 3'-epilutein.

In animal tissues and liquors 3'-epilutein is more widespread, but unfortunately, always in very low concentration; see the overview provided in T. Matsuno, T. Maoka, M. Katsuyama, T. Hirono, Y. Ikuno, M. Shimizu, T. Komori, *Comp. Biochem. Physiol.* B85, 77 (1986). Recent findings with respect to 3'-epilutein concern:—human plasma [F. Khachik, G. R. Beecher, M. B. Goli, W. R. Lusby, J. C. Smith jr., *Anal. Chem.* 64, 2111 (1992)],—the skin of trouts [M. C. Vecchi, G. Englert, H. Mayer, *Helv. Chim. Acta*, 65, 1950 (1982)];—human breast milk [F. Khachik, C. J. Spangler, J. C. Smith jr., L. M. Canfield, A. Steck, H. Pfander, *Anal. Chem.* 69, 1873 (1997)].

The small quantities found made any preparative isolation prohibitively costly.

Synthesis of several epiluteins starting from lower synthons are described in H. Mayer "*Carotenoid Chemistry & Biochemistry*" Ed. G. Britton, T. W. Goodwin, Pergamon Press, London 1982, pag. 55, ff for various epimers, but not for 3'-epilutein itself.

A conversion of lutein into 3'-epilutein via 3'-O-didehydrolutein (oxolutein, VI) followed by a hydride reduction was described for the first time in R. Buchecker, C. H. Eugster, A. Weber, *Helv. Chim. Acta* 61, 1962 (1978). It leads to a mixture of I:V with a ratio of 1:2 (I:V). The separation of both stereoisomers is easily performed by HPLC. Pure V was isolated by column-chromatography and fully characterized by melting point and relevant spectra.

In *Caltha palustris* 3'-epilutein is accompanied by lutein and oxolutein (VI) (see FIG. 6) [R. Buchecker, C. H. Eugster, *Helv. Chim. Acta* 62, 2817 (1979)], and [E. M ärki-Fischer, C. H. Eugster, *Helv. Chim. Acta* 73, 1205 (1990)].

This fact points to a special enzymic oxido-reduction in the plant.

Epimerization Reactions at C-3' in Lutein.

The so-called "acid-lability" of lutein has long been recognized, see for example F. W. Quackenbush, H. Steebock, W. A. Peterson, *J. Amer. Chem. Soc.* 60, 2937 (1938); H. H. Strain, "Leaf Xanthophylls", Carnegie Inst. Of Plant Biology, Washington, 1938, pag. 87.; A. L. Curl, *Food Research* 21, 689 (1956), but any identification of the products formed was lacking. Only Zechmeister et al, were able to identify some of the products they had produced by some very special elimination reactions [L. Zechmeister, J. W. Sease, *J. Amer. Chem. Soc.* 65, 1951 (1943); F. J. Petracek, L. Zechmeister, *J. Amer. Chem. Soc.* 78, 1427 (1956); L. Zechmeister, "*Fortschr. Chem. Org. Naturstoffe*", 15, 31(1958)].

From a modern point of view, specific reactions at C-3'-OH of lutein are due to the specific nature of the allylic alcohol. In mechanistic terms its reaction with various electrophiles has to be classified as an $S_N1$-type. This includes a planar allylic cation (VII, see FIG. 7) as intermediate which is prone to an attack by nucleophiles either from "above" or "below" and both at C(3') or C(5'). However, in contrast to J. Szabolcs, *Acta Chim. Hung.* 61, 301 (1969), applicants never found C(5')-substituted products in their experiments.

In all likelihood, all of these reactions are reversible.

From mechanistic considerations it is clear that the orientation of an attack of the nucleophile depends also on steric factors, therefore, applicants always have to expect more than one product; either one with a cis or a transrelation to the substituent at C(6').

Whether the reaction is thermodynamically or kinetically controlled is as yet unclear.

At this point a remark has to be made about the so called Mitsunobu-reaction. It works in the sense of an $S_N2$-reaction with the result of a clean epimerization at the center concerned. Such a reaction with the intention of preparing 3'-epilutein from (unprotected) lutein has been published by H. R. Sliwka, S. Liaaen-Jensen, *Acta Chem. Scand.* B41, 518 (1987). Besides many by-products, only 0.3% of 3'-epilutein could be isolated.

Finally performing acid-catalyzed reactions of lutein in the presence of the nucleophillic solvent methanol allowed the isolation of lutein-3'-methylether (VIII see FIG. 8) [S. Liaaen-Jensen, S. Hertzberg, *Acta Chem. Scand.* 20, 1703 (1966)], but neither its stereochemistry nor the structure of other possible isomers were clarified.

In fact, such a reaction is, as discussed above, not stereoselective.

Applicants own experiments showed the presence of both cis- and trans-methylethers in a ratio of 2:1 [C. H. Eugster, Report by E-Mail on Nov. 11, 1999 to Industrial Orgánica, S.A. de C.V., Monterrey, México]. They can be easily separated on a HPLC column.

Based on these facts, applicants were astounded to realize that until now, no single researcher has made use of the very common nucleophile $OH^-$ in an $S_N1$-reaction with lutein. From this fact it follows that a solution of lutein in a solvent that is also miscible with water, a reaction at $C(3')^+$ with water should occur during the addition of an aqueous solution of a strong acid with the formation of two stereoisomers, namely lutein (I) and 3'-epilutein (V). An excellent solvent for such a reaction is tetrahydrofurane in which lutein is easily soluble. Another very important fact is to avoid mineral acids whose anions show appreciable nucleophilic activity. Therefore, aqueous sulfuric acid or perchloric acid, etc., were Applicants first choice.

With a concentrate from Tagetes, containing 39% of lutein, Applicants were able to obtain a mixture of lutein and 3'-epilutein in a ratio of about 1:4 to about 1:5.5.

Other combinations could include e.g. glycolethers, dichloromethane, benzene, with aqueous sulfuric acid, perchloric acid, trifluoroacetic acid, ion-exchanger, etc.

The Epsilon-beta Rearrangement with 3'-epilutein (V) into (3R,3'R)-zeaxanthin (III)

In the case of 3'-epilutein possibly no assistance of $C(3')$—$O^-$ to the abstraction of H—C(6') takes place for stereochemical reasons, so a change of the conditions disclosed in U.S. Pat. No. 5,523,494, issued Jun. 4, 1996 to Torres-Cardona et al. was necessary.

In fact, under modified conditions, Applicants were able to obtain (3R,3'R)-zeaxanthin (III) in good yield and with a high optical purity from the mixture of 3'-epilutein with lutein. The residual lutein led to minor contamination of the product with meso-zeaxanthin (II).

However, until the present time, the proportion of (3R-3'R) stereoisomers of zeaxanthin obtained from the conventional saponification processes, is at most 3–7% of the total xanthophylls.

Applicants have had the foresight to realize the convenience of employing an optically active zeaxanthin for enhancing the color pigmentation of the broiler skin and egg yolks, as well as its use in the treatment or prevention of macula degeneration in humans.

SUMMARY OF THE INVENTION

It is therefore a main object of the present invention, to provide a process for obtaining 3'-epilutein, from a lutein-containing extract.

It is also a main object of the present invention, to provide a process for obtaining 3'-epilutein, of the above-disclosed nature, by reacting a lutein-containing extract, with an inorganic or organic acid, whose anions possess a very low nucleophilicity in order to obtain 3'-epilutein.

It is additionally an object of the present invention, to provide a process for obtaining 3'-epilutein, of the above-disclosed nature, from which optically active zeaxanthin is obtained.

It is a further main object of the present invention, to provide a process for obtaining optically active zeaxanthin, from 3'-epilutein.

It is still a main objective of the present invention, to provide a process for obtaining optically active zeaxanthin, by reacting 3'-epilutein with a strongly alkaline aqueous solution.

BRIEF DESCRIPTION OF THE DRAWINGS

FIG. 8, shows the reaction of lutein with electrophiles for achieving a planar allylic cation as desoxiluteins(VII); and FIG. 9, shows the acid-catalyzed reactions of lutein in the presence of the nucleophillic solvent methanol allowing for the isolation of lutein-3'-methylether (VIII).

DETAILED DESCRIPTION OF THE INVENTION

Figure 1:
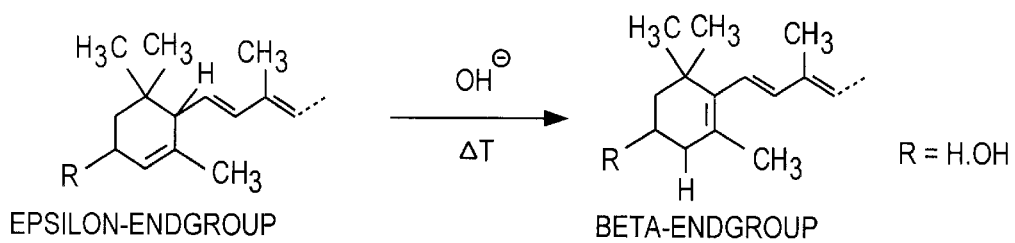
FIG. 1, shows the isomerization of an epsilon-endgroup in a carotenoid molecule, with extension of the length of the polyene-chain from originally 10 to 11 conjugated double bonds.
Figure 2:
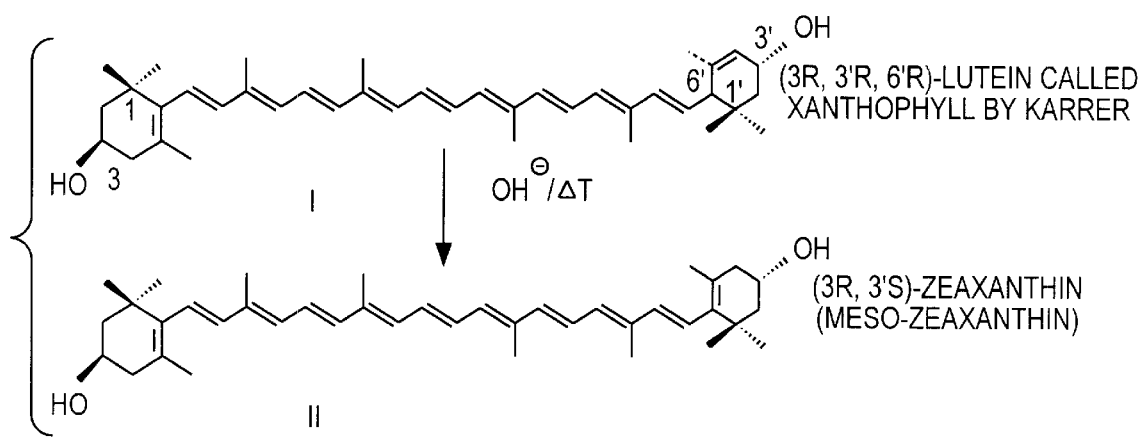
FIG. 2, is the formula of lutein (I) having a 3R, 3'R, 6'R chirality.
Figure 3:
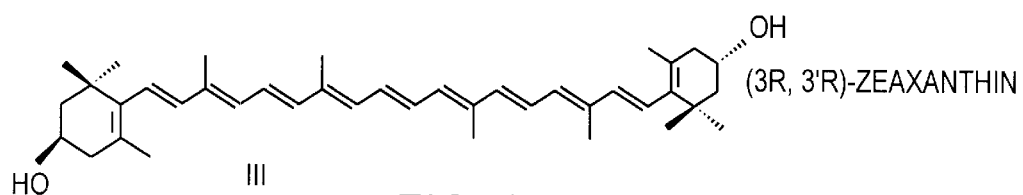
FIG. 3, is the formula of the zeaxanthin(meso-zeaxanthin) (II) having a (3R,3'S) chirality.
Figure 4:
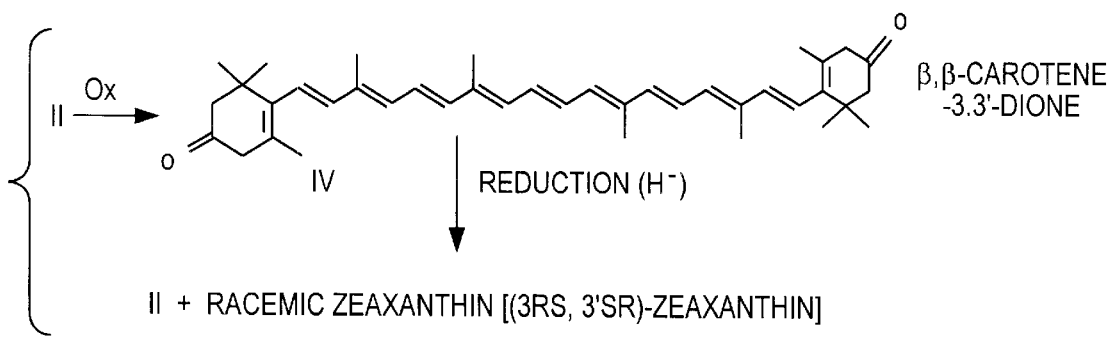
FIG. 4, is the formula of the (3R,3'R)-zeaxanthin (II).
Figure 5:
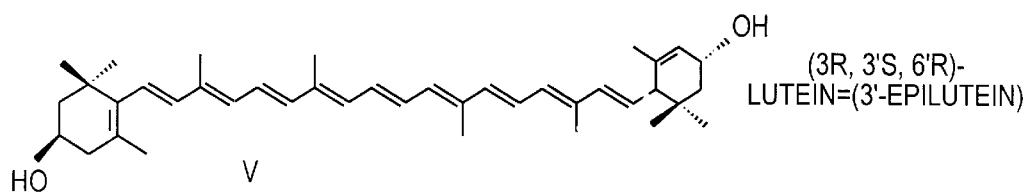
FIG. 5, shows the oxidation of the meso-zeaxanthin(II) into dioxocompound (IV).
Figure 6:
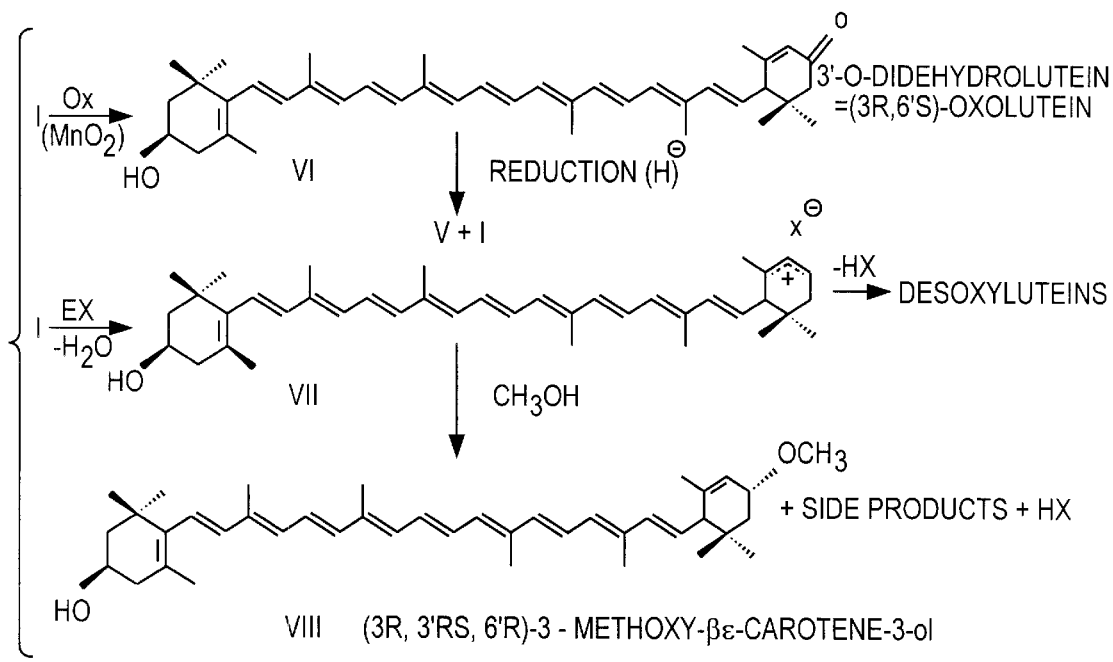
FIG. 6, is the formula of the 3'-epilutein.
Figure 7:
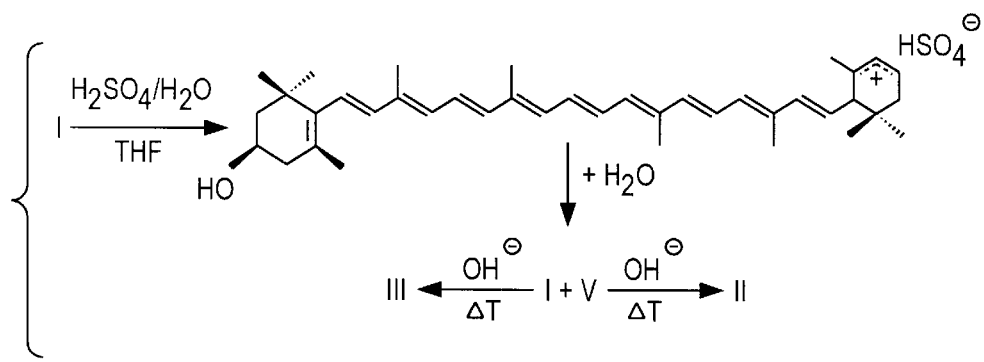
FIG. 7, shows the conversion of lutein into 3'-epilutein via 3'O-Didehydrolutein (oxolutein VI).

By way of a preferred specific embodiment of the invention, the process for obtaining 3'-epilutein, comprises:

reacting 5 gr. of an enriched lutein solution, containing 39% of pure lutein, with 2 ml of an aqueous solution of 1N sulfuric acid, in tetrahydrofurane as a solvent;

stirring the reacting mixture at room temperature;

neutralizing the solution after about 14 hours of reaction with ammonium hydroxide and 3'-epilutein;

partitioning the solution, with methylene dichloride;

washing the 3'-epilutein with water and with a solution of sodium chloride;

drying the 3'-epilutein by means of anhydrous sodium sulfate and evaporation, to yield 1.22 gr. of 3'-epilutein crystals; and purifying the crystals by chromatography in a silica-gel column with $CH_2Cl_2$/ethyl-acetate obtaining a main zone having red-orange hue.

The following table includes the results obtained from some examples of the process carried out under different operating conditions, by using pure lutein; a lutein concentrate, produced by Industrial Organica, S.A., de C.V., a Mexican Corporation, under the trademark Hi-Fil; a saponified marigold oleoresin, and a marigold oleoresin.

EXAMPLES

| RAW MATERIAL | % LUTEIN | % EPILUTEIN | % CONV | Rxn MEDIA | ACID [N] | TEMP. | TIME (hr) |
| --- | --- | --- | --- | --- | --- | --- | --- |
| Pure lutein | 99.22 | 84.53 | 92.9 | Tetrahydrofurane | 1X | Room Temp. | 43 |
| Hi-Fil | 90.99 | 49.54 | 54.4 | Tetrahydrofurane | 1X | Room Temp. | 72 |
| Hi-Fil | 90.99 | 9.34 | 10.3 | Dimethylformamide | 1X | Room Temp. | 14 |
| Hi-Fil | 90.99 | 1.2 | 1.3 | Dimethylsulfoxide | 1X | Room Temp. | 48 |
| Hi-Fil | 90.99 | 43.65 | 48 | Tetrahydrofurane | 2X | 50° C. | 10 |
| Hi-Fil | 90.99 | 41.32 | 45.4 | Tetrahydrofurane | 1X | 50° C. | 5 |
| Hi-Fil | 90.99 | 8.59 | 9.4 | Hexane | 1X | Room Temp. | 36 |
| Saponified marigold oleoresin | 80.63 | 41.63 | 46 | Tetrahydrofurane | 1X | Room Temp. | 20 |
| Marigold oleoresin | 74.24 | 4.99 | 6.6 | Tetrahydrofurane | 1X | 50° C. | 48 |

From the above process examples, it can be seen that crystals of 3'-epilutein were obtained at conversion percentages ranging between 1.3% to 92.9%.

Applicants have furthermore foreseen the convenience of starting from said 3'-epilutein to obtain optically active (3R,3'R)-zeaxanthin, for enhancing the color pigmentation of the broiler skin and egg yolks, as well as its use in the treatment or prevention of the macula degeneration in humans.

Therefore, the process for obtaining optically active 3R,3'R-zeaxanthin by isomerization of 3'-epilutein crystals, comprises reacting said 3'-epilutein crystals, with a strongly alkaline solution, such as sodium hydroxide, potassium hydroxide, sodium carbonate, ammonium hydroxide, ammonia, or mixtures thereof.

What is claimed is:

1. A process for obtaining 3'-epilutein, comprising:

reacting a lutein-containing extract with an aqueous inorganic or organic acid whose anions possess a very low nucleophilicity in the presence of an organic aprotic media, to obtain a 3'-epilutein solution.

2. The process according to claim 1, wherein the inorganic or organic acid is a strong mineral or organic acid, selected from the group consisting of sulfuric acid, hydrochloric acid, trifluoroacetic acid, perchloric acid, tetrafluoroboric acid, or mixtures thereof.

3. The process according to claim 1, comprising slowly adding the strong inorganic or organic acid under agitation at a temperature between ambient temperature and about 50° C.

4. The process according to claim 1, wherein the organic aprotic media is selected from tetrahydrofurane, hexane, dimethylformamide, dimethylsulfoxide, glycolethers, or mixtures thereof.

5. The process according to claim 1, comprising neutralizing the solution with an alkali.

6. The process according to claim 1 comprising neutralizing the solution with ammonium hydroxide.

7. The process according to claim 1, comprising partitioning a 3'-epilutein solution by means of an organic media.

8. The process according to claim 1, comprising partitioning the 3'-epilutein solution with an organic solvent.

9. The process according to claim 1, comprising partitioning the 3'-epilutein solution with methylene dichloride.

10. The process according to claim 1, comprising washing the 3'-epilutein solution.

11. The process according to claim 1, comprising washing the 3'-epilutein solution with water.

12. The process according to claim 1, comprising washing the 3'-epilutein solution with a solution of sodium chloride.

13. The process according to claim 1, comprising drying the 3'-epilutein solution with anhydrous sodium sulfate.

14. The process according to claim 1, comprising crystallizing the 3'-epilutein by solvent evaporation to obtain 3'-epilutein crystals.

15. The process according to claim 1, comprising purifying the 3'-epilutein crystals by chromatography.

16. The process according to claim 1, comprising purifying the 3'-epilutein crystals by chromatography in a column of silica gel.

17. The process according to claim 1, wherein the reaction time is from about 4 hours to about 130 hours.

18. The process according to claim 1, comprising reacting an extract containing about 1% to about 99.22% by weight of lutein with 1N sulfuric acid, in a ratio of about 1:1 to about 1:8.

19. A process for obtaining 3'-epilutein, comprising:

reacting a lutein-containing extract with an aqueous solution of sulfuric acid, in the presence of tetrahydrofurane, to obtain a solution of 3'-epilutein;

neutralizing the solution with ammonium hydroxide;

partitioning the 3'-epilutein by means of dichloromethane;

washing the 3'-epilutein solution with water and with a solution of sodium chloride;

drying the 3'-epilutein solution by means of anhydrous sodium sulfate;

crystallizing the 3'-epilutein by evaporation, to obtain 3'-epilutein crystals; and purifying the 3'-epilutein crystals by chromatography in a column of silica gel.

20. The process according to claim 19, wherein the lutein containing extract is reacted with an aqueous solution of sulfuric acid, by slowly adding the sulfuric acid under agitation, at a temperature between the ambient temperature and about 50° C., during a period of from about 4 hours to about 130 hours.

21. The process according to claim 19, comprising reacting the extract containing about 1% to about 99.22% by weight of lutein with 1N sulfuric acid, in a ratio of about 1:1 to about 1:8.

22. A process for obtaining optically active (3R,3'R)-zeaxanthin, comprising:

reacting a lutein-containing extract with an aqueous solution of an inorganic or organic acid in the presence of an organic aprotic media, to obtain a 3'-epilutein solution;

neutralizing the solution with an alkali; and reacting 3'-epilutein crystals, with a strongly alkaline aqueous solution.

23. A process for obtaining optically active (3R,3'R)-zeaxanthin, according to claim 22, wherein the inorganic or organic acid is a strong mineral or organic acid, selected from the group consisting of sulfuric acid, hydrochloric acid, trifluoroacetic acid, perchloric acid, tetrafluoroboric acid, or mixtures thereof.

24. A process for obtaining optically active (3R,3'R)-zeaxanthin, according to claim 22, wherein the organic aprotic media is selected from tetrahydrofurane, hexane, dimethylformamide, dimethylsulfoxide, glycolethers, or mixtures thereof.

25. The process according to claim 14, comprising purifying the 3'-epilutein crystals by chromatography.

26. The process according to claim 14, comprising the 3'-epilutein crystals by chromatography in a column of silica gel.

* * * * *